United States Patent

Thompson et al.

[11] Patent Number: 5,908,860
[45] Date of Patent: Jun. 1, 1999

[54] BICYCLIC COMPOUNDS WITH PHARMACEUTICAL ACTIVITY

[75] Inventors: Mervyn Thompson, Harlow; John Morris Evans, Roydon; Neil Upton, Harlow; Wai Ngor Chan, Epping; Kuok Keong Vong, Sawbridgeworth, all of United Kingdom; Robert Nicholas Willette, Pottstown, Pa.

[73] Assignees: SmithKline Beecham plc,, Brentford, United Kingdom; SmithKline Beecham Corporation, Philadelphia, Pa.

[21] Appl. No.: 08/448,518
[22] PCT Filed: Dec. 8, 1993
[86] PCT No.: PCT/GB93/02512
 § 371 Date: Jul. 6, 1995
 § 102(e) Date: Jul. 6, 1995
[87] PCT Pub. No.: WO94/13656
 PCT Pub. Date: Jun. 23, 1994

[30] Foreign Application Priority Data

Dec. 11, 1992 [GB] United Kingdom .................. 9225881
Dec. 11, 1992 [GB] United Kingdom .................. 9225956
Dec. 11, 1992 [GB] United Kingdom .................. 9225957
Dec. 11, 1992 [GB] United Kingdom .................. 9225963
Dec. 11, 1992 [GB] United Kingdom .................. 9225964

[51] Int. Cl.$^6$ ...................... A61K 31/35; C07D 311/06; C07D 315/00
[52] U.S. Cl. .......................... 514/456; 549/399; 549/404; 549/407; 549/415; 549/424
[58] Field of Search .................... 514/456; 549/399, 549/404, 407, 415, 424

[56] References Cited

U.S. PATENT DOCUMENTS 5,624,954  4/1997  Evans et al. .

FOREIGN PATENT DOCUMENTS 0 126 311  11/1984  European Pat. Off. .
0 205 292  12/1986  European Pat. Off. .
0 339 562  11/1989  European Pat. Off. .

*Primary Examiner*—Johann Richter
*Assistant Examiner*—Taofiq A. Solola
*Attorney, Agent, or Firm*—Mary E. McCarthy; Stephen Venetianer; Charles M. Kinzig

[57] ABSTRACT

This invention relates to the method of treatment and/or prophylaxis of anxiety and/or disorders treatable and/or preventable with anti-convulsive agents, such as epilepsy, using compounds of the formula (Ia):

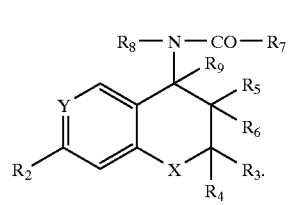

2 Claims, No Drawings

BICYCLIC COMPOUNDS WITH PHARMACEUTICAL ACTIVITY

This appl. is a 371 of PCT/GB93/02512 filed Dec. 8, 1993.

This invention relates to a novel method of treatment, to novel compounds and to the preparation of compounds for use in such a method.

European Published Patent Application No. 0126311 discloses substituted benzopyran compounds having blood pressure lowering activity, including 6-acetyl-trans-4-(4-fluorobenzoylamino)-3,4-dihydro-2,2-dimethyl-2H-1-benzopyran-3-ol.

Also EP-A-0 376 524, EP-A-0 205 292, EP-A-0 250 077, EP-A-0 093 535, EP-A-0 150 202, EP-A-0 076 075 and WO/89/05808 (Beecham Group plc) describe certain benzopyran derivatives which possess anti-hypertensive activity.

EP-A-0 350 805 (Biersdorf), EP-A-0 277 611, EP-A-0 277612, EP-A-0 337 179 and EP-A-0 355 565 (Hoechst Aktiengesellschaft); EP-A-415 065 (E. Merck) and EP-A-450415 (Squibb), EP-A-0 466 131 (Nissan Chemical Industries Ltd), EP-A-0339562 (Yoshitomi Pharmaceuticals), EP-A-0482934, EP-A-0296975, JO-2004-791 and WO\89\07103 also describe certain benzopyran derivatives which are believed to possess anti-hypertensive activity.

PCT/Application WO 92/22293 (SmithKline Beecham plc; unpublished at the priority date), describes certain fluorobenzoyl benzopyrans having inter alia anxiolytic and anti-convulsant activity.

EP-A-0 430 621 and EP-A-0 385 584 (Beecham Group plc) describe the resolution of certain intermediates useful in the preparation of the compounds described in the above mentioned patent applications.

EP-A-0 194 885 (E. Lilly) describes certain amino substituted benzopyran derivatives possessing anti-convulsant activity.

It has now been surprisingly found that certain compounds of formula (Ia) possess anxiolytic and anti-convulsant activity, and are also believed to have utility in the treatment or prevention of mania, depression and the effects associated with withdrawal from substances of abuse, and that compounds of formula (I) have utility in the treatment or prevention of disorders resulting from sub-arachnoid haemorrhage, neural shock, cerebral ischaemia, Parkinson's Disease, migraine and/or psychosis.

Accordingly, the present invention provides a method of treatment and/or prophylaxis of disorders resulting from sub-arachnoid haemorrhage, neural shock, cerebral ischaemia, Parkinson's Disease, migraine and/or psychosis, in mammals, especially humans which comprises administering to the sufferer in need thereof an effective or prophylactic amount of a compound of formula (I) or pharmaceutically acceptable salt thereof:

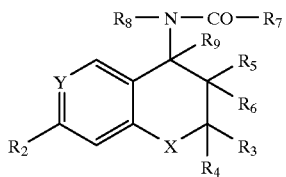

(I)

wherein:
either Y is N and $R_2$ is hydrogen, or Y is C—$R_1$
where:

either one of $R_1$ and $R_2$ is hydrogen and the other is selected from the class of hydrogen, $C_{3-8}$ cycloalkyl, $C_{1-6}$ alkyl optionally interrupted by oxygen or substituted by hydroxy, $C_{1-6}$ alkoxy or substituted aminocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$—, CH(OH), $SO_2$, SO, $CH_2$—O, or CONH, or a group $CF_2H$—A'— where A' is oxygen, sulphur, SO, $SO_2$, $CF_2$ or CFH; trifluoromethoxy, $C_{1-6}$ alkylsulphinyl, perfluoro $C_{2-6}$ alkylsulphonyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, phosphono, arylcarbonyloxy, heteroarylcarbonyloxy, arylsulphinyl, heteroarylsulphinyl, arylsulphonyl, heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, any amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl; or $R_1$ and $R_2$ together are —(CH$_2$)$_4$—or —CH=CH—CH=CH—, or form an optionally substituted triazole or oxadiazole ring;

one of $R_3$ and $R_4$ is hydrogen or $C_{1-4}$ alkyl and the other is $C_{1-4}$ alkyl, $CF_3$ or $CH_2$ $X^a$, where $X^a$ is fluoro, chloro, bromo, iodo, alkoxy, hydroxy, $C_{1-4}$ alkylcarbonyloxy, —S—$C_{1-4}$ alkyl, nitro, amino optionally substituted by one or two $C_{1-4}$ alkyl groups, cyano or $C_{1-4}$ alkoxycarbonyl or $R_3$ and $R_4$ together are $C_{2-5}$ polymethylene optionally substituted by $C_{1-4}$ alkyl;

$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;

$R_7$ is heteroaryl or phenyl both of which are; optionally substituted one or more times independently with a group or atom selected from chloro, fluoro, bromo, nitro, amino optionally substituted by $C_{1-4}$ alkyl, cyano azido, $C_{1-4}$ alkyl, $C_{1-4}$ alkoxy, trifluoromethoxy and trifluoromethyl;

$R_8$ is hydrogen; $C_{1-6}$ alkyl, $OR_9$ or $NHCOR_{10}$ wherein $R_9$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl, $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$alkyl, $C_{1-6}$ alkoxycarbonyl-$C_{1-6}$-alkyl, aryl or heteroaryl; the $R_8$—N—CO—$R_7$ group being trans to the $R_5$ group; and X is oxygen or $NR_{10}$ where $R_{10}$ is hydrogen or $C_{1-6}$ alkyl.

The present invention further provides a method of treatment and/or prophylaxis of anxiety, mania, depression, the effects associated with withdrawal from substances of abuse such as cocaine, nicotine, alcohol and benzodiazepines, and/or disorders treatable preventable with anti-convulsive agents, such as epilepsy; comprising administering to the sufferer in need thereof an effective or prophylactic amount of a compound of formula (Ia) or pharmaceutically acceptable salt thereof:

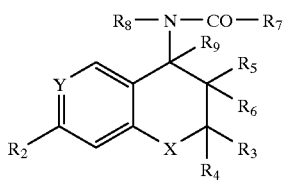

wherein:
either Y is N and $R_2$ is hydrogen, or Y is C—$R_1$ where: either one of $R_1$ and $R_2$ is hydrogen and the other is selected from a first group:
  a) consisting of hydrogen, $C_{3-8}$ cycloalkyl, $C_{1-6}$ alkyl optionally interupted by oxygen or substituted by hydroxy, $C_{1-6}$ alkoxy or substituted arninocarbonyl, $C_{1-6}$ alkylcarbonyl, $C_{1-6}$ alkoxycarbonyl, $C_{1-6}$ alkylcarbonyloxy, $C_{1-6}$ alkoxy, nitro, cyano, halo, trifluoromethyl, $CF_3S$, or a group $CF_3$—A—, where A is —$CF_2$—, —CO—, —$CH_2$—, or CH(OH), trifluoromethoxy, $C_{1-6}$ alkylsulphinyl, $C_{1-6}$ alkylsulphonyl, $C_{1-6}$ alkoxysulphinyl, $C_{1-6}$ alkoxysulphonyl, aryl, heteroaryl, arylcarbonyl, heteroarylcarbonyl, arylsulphinyl, heteroarylsulphinyl, arylsulphonyl, heteroarylsulphonyl in which any aromatic moiety is optionally substituted, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, any amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)$NNH_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl; or a second group:
  b) consisting of $CF_3A$; where A is $SO_2$ or CONH, or $C_{2-6}$ perfluoroalkylsulphonyl or a group $CF_2H$—A'— where A' is oxygen, sulphur, SO, $SO_2$, $CF_2$ or CFH; phosphono, arylcarbonyloxyl or heteroarylcarbonyloxy; or $R_1$ and $R_2$ together represent —$(CH_2)_4$— or —CH=CH—CH=CH—, or form an optionally substituted triazole or oxadiazole ring;
one of $R_3$ and $R_4$ is hydrogen or $C_{1-4}$ alkyl and the other is $C_{1-4}$ alkyl $CF_3$ or $CH_2 X^a$, where $X^a$ is fluoro, chloro, bromo, iodo, alkoxy, hydroxy, $C_{1-4}$ alkyl-carbonyloxy, —S—$C_{1-4}$ alkyl, nitro, amino optionally substituted by one or two $C_{1-4}$ alkyl groups, cyano or $C_{1-4}$ alkoxycarbonyl or $R_3$ and $R_4$ together are $C_{2-5}$ polymethylene optionally substituted by $C_{1-4}$ alkyl;
$R_5$ is $C_{1-6}$ alkylcarbonyloxy, benzoyloxy, $ONO_2$, benzyloxy, phenyloxy or $C_{1-6}$ alkoxy and $R_6$ and $R_9$ are hydrogen or $R_5$ is hydroxy and $R_6$ is hydrogen or $C_{1-2}$ alkyl and $R_9$ is hydrogen;
$R_7$ is heteroaryl or phenyl; optionally substituted one or more times with a group or groups selected from azido, chloro, fluoro, bromo, iodo, nitro, amino optionally substituted once or twice by $C_{1-4}$ alkyl; $C_{1-4}$ alkyl, cyano, $C_{1-4}$ alkoxy, trifluoroalkyl and trifluoromethyl;

$R_8$ is selected from either a first group;
  c) in which $R_8$ is hydrogen or $C_{1-6}$ alkyl, or a second group
  d) in which $R_8$ is $OR_9$ or $NHCOR_{10}$ wherein $R_9$ is hydrogen, $C_{1-6}$ alkyl, formyl, $C_{1-6}$ alkanoyl, aroyl or aryl-$C_{1-6}$ alkyl and $R_{10}$ is hydrogen, $C_{1-6}$ alkyl $C_{1-6}$ alkoxy, mono or di $C_{1-6}$ alkyl amino, amino, amino-$C_{1-6}$ alkyl, hydroxy-$C_{1-6}$ alkyl, halo-$C_{1-6}$ alkyl, $C_{1-6}$ acyloxy-$C_{1-6}$ alkyl, $C_{1-6}$ alkoxycarbonyl-$C_{1-6}$-alkyl, aryl or heteroaryl;
the $R_8$—N—CO—$R_7$ group being trans to the $R_5$ group;
and X is oxygen or $NR_{10}$ where $R_{10}$ is hydrogen or $C_{1-6}$ alkyl; with the proviso that when $R_7$ is phenyl substituted exclusively with fluoro, $R_1\backslash R_2$ and $R_8$ are not simultaneously selected from groups a) and c) respectively.

Aryl whenever mentioned herein includes but is not limited to phenyl and naphthyl.

Heteroaryl whenever mentioned herein includes a 5- or 6-membered monocyclic or 9- or 10-membered bicyclic of which 5- or 6-membered monocyclic heteroaryl is preferred. In addition, 5- or 6-membered monocyclic or 9- or 10-membered bicyclic heteroaryl preferably contains one, two or three heteroatoms which are selected from the class of oxygen, nitrogen and sulphur and which, in the case of there being more than one heteroatom, are the same or different. Examples of 5- or 6-membered monocyclic heteroaryl containing one, two or three heteroatoms which are selected from the class of oxygen, nitrogen and sulphur include furyl, thienyl, pyrryl, oxazolyl, thiazolyl, imidazolyl and thiadiazolyl, and pyridyl, pyridazyl, pyrimidyl, pyrazolyl and triazolyl. Preferred examples of such groups include furanyl, thienyl, pyrryl and pyridyl, in particular 2- and 3-furyl, 2- and 3-pyrryl, 2- and 3-thienyl, and 2-, 3- and 4-pyridyl. Examples of 9- or 10-membered bicyclic heteroaryl containing one, two or three heteroatoms which are selected from the class of oxygen, nitrogen and sulphur include benzofuranyl, benzothienyl, indolyl and indazolyl, quinolyl and isoquinolyl, and quinazolyl. Preferred examples of such groups include 2- and 3-benzofuryl, 2- and 3-benzothienyl, and 2- and 3-indolyl, and 2- and 3-quinolyl.

Suitable examples of groups or atoms for optional substitution especially of aryl and heteroaryl include one, two or three substituents independently selected from $C_{1-4}$ alkyl, $C_{1-4}$ alkoxy, halo (such as fluoro, chloro, bromo), hydroxy, nitro, cyano and $SO_nH$, where n=0 to 2.

Preferably $R_1$ substituents are cyano, methoxy, trifluoromethoxy, chloro, trifluoromethyl, ethylcarbonyl, acetyl, hydrogen, methyl, ethyl, iso-propyl, tertiarybutyl, nitro, $C_2F_5$, methoxycarbonyl, phenylsulphonyl, phenyl, fluoro, iodo, cyclopentyl, amninocarbonylmethyl and 1-hydroxyethyl. More preferably $R_1$ is cyano, ethyl, acetyl, or nitro. Most preferably $R_1$ is acetyl.

Preferably $R_2$ is hydrogen.

Preferably $R_3$ and $R_4$ are both methyl.

Preferably $R_5$ is hydroxy and $R_6$ and $R_9$ are hydrogen or $R_5$ is hydroxy, $R_6$ is $C_{1-2}$ alkyl and $R_9$ is hydrogen, more preferably $R_5$ is hydroxy and $R_6$ and $R_9$ are hydrogen.

Preferably $R_7$ is 2-pyridyl, 2-furyl, 5-chloro-2-furyl, 4-chlorophenyl, 4-nitrophenyl, 4-aminophenyl, 4-trifluoromethylphenyl, phenyl, 4-cyanophenyl, 3-nitrophenyl, 3,4-dichlorophenyl, 2-iodophenyl, 3-bromo-4-fluorophenyl, 3-trifluoromethyl-4-fluorophenyl, 4-bromophenyl, 3-fluoro-4-methylphenyl, 3-fluoro-4-methoxyphenyl, 3-chloro-4-fluorophenyl, 3-bromophenyl, 4-fluoro-3-methyl phenyl, 5-bromo-2-furyl, 2-azidophenyl, 3-azidophenyl, 3-chlorophenyl, 3-trifluoromethylphenyl, 3-iodophenyl, 2-nitrophenyl, 2-chlorophenyl, 3-cyanophenyl, 2-aminophenyl, 3-trifluoromethoxyphenyl, 2,3-dichlorophenyl, 2-chloro-4-fluorophenyl, 2-trifluoromethylphenyl, 3-chlorophenyl, 3-chloro-2-thiophenyl, 5-bromo-2-thiophenyl, 3,5-dibromophenyl, 2-chloro-6-fluorophenyl, 3-chloro-2-fluorophenyl, 2,6-dichlorophenyl, 2-azido-4-fluorophenyl, 2-methyl-phenyl, 4-methylphenyl, 2-chloro-3-nitrophenyl, 2-chloro-5-nitrophenyl, 2-methoxyphenyl, 2-chloro-4-methoxyphenyl, 4-fluorophenyl, 3-fluorophenyl or 2-pyrazinyl.

Most preferably $R_7$ is 2-chlorophenyl or 2-chloro-4-fluorophenyl.

Preferably $R_8$ is hydrogen or $C_{1-4}$ alkyl, more preferably $R_8$ is hydrogen, methyl or ethyl. Most preferably $R_8$ is hydrogen.

Preferably X is oxygen.

It should be appreciated that the compounds of formula (I) may have chiral carbon atoms at positions 2, 3 and 4 and therefore may exist as enantiomers. The present invention extends to each enantiomer and to mixtures thereof including racemates. Preferably the compounds of formula (Ia) are the 4S, 3R enantiomers when used in the treatment of Parkinson's Disease, migraine, psychosis and/or mania, and/or depression and/or the effects associated with withdrawal from substances of abuse such as cocaine, nicotine, alcohol and benzodiazepines, and/or disorders treatable and/or preventable with anti-convulsive agents, such as epilepsy.

Preferably the compounds of formula (I) are the 3S, 4R enantiomers when used in the treatment of disorders resulting from sub-arachnoid hemorrhage or neural shock. It should be appreciated that a particularly preferred compound for use in treating these disorders is trans-6-cyano-4R-(3-fluorobenzoylamino)-3,4-dihydro-2,2-dimethyl-2H-1-benzopyran-3S-ol which is example 22 in PCT/GB92/01045.

It should also be appreciated that certain $R_1$ substituents also have chiral centres and therefore may exist as enantiomers. The present invention extends to each enantiomer and to mixtures thereof including racemates.

It should be appreciated that the compound of formula (I) and (Ia), or a pharmaceutically acceptable salt thereof also includes solvates of such compounds, such as for example the hydrate.

The present invention further provides a compound of formula (Ia), or a pharmaceutically acceptable salt thereof as hereinbefore defined which exists predominantly in the 4S, 3R enantiomeric form.

It should be appreciated that the term "exists predominantly in the 4S, 3R enantiomeric form" means that there is greater than 50% of the 4S, 3R enantiomer present compared to the 4R, 3S enantiomer. More preferably there is greater than 60% of the 4S, 3R enantiomer present, yet more peferably greater than 70% of the 4S, 3R enantiomer presence, even more preferably greater than 80% of the 4S, 3R enantiomer present and more preferably still greater than 90% of the 4S, 3R enantiomer present. Most preferably there is greater than 95% of the 4S, 3R enantiomer compound to the 4R, 3S enantiomer.

The present invention also provides use of a compound of formula (Ia) or a pharmaceutically acceptable salt thereof which exists predominantly in the 4S, 3R enantiomeric form as a therapeutic agent, in particular to the use of such a compound in any of the utilities mentioned herein.

The present invention also provides a pharmaceutical composition comprising a compound of formula (Ia), or a pharmaceutically acceptable salt thereof which exists predominantly in the 4S, 3R enantiomeric form, admixed with a pharmaceutically acceptable carrier.

The administration to the mammal may be by way of oral or parenteral administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50 100, 200, 300 or 400 mg of the active compound. Unit doses will normally be administered once or more than once per day, for example 12, 3, 4, 5 or 6 times a day, more usually 1 to 4 times a day, such that the total daily dose is normally in the range, for a 70 kg adult of 1 to 1000 mg, for example 50 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) or (Ia) is administered in the form of a unit-dose composition, such as a unit dose oral, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

The present invention further provides a pharmaceutical composition for use in treatment and/or prophylaxis of disorders resulting from sub-arachnoid haemorrhage or neural shock and/or cerebral ischaenia, and/or Parkinson's Disease, migraine or psychosis, in mammals, especially humans which comprises a compound of formula (I), or a pharmaceutically acceptable salt thereof, and a pharmaceutically acceptable carrier.

The present invention further provides a pharmaceutical composition for use in the treatment and/or prophylaxis of anxiety, mania, depression, the effects associated with withdrawal from substances of abuse such as cocaine, nicotine, alcohol and benzodiazepines and/or disorders treatable or preventable with anti-convulsive agents, such as epilepsy; which comprises a compound of formula (Ia), or a pharmaceutically acceptable salt thereof, and a pharmaceutically acceptable carrier.

In a further aspect the invention provides the use of a compound of formula (I), or a pharmaceutically acceptable salt thereof, for the manufacture of a medicament for the treatment and/or prophylaxis of disorders resulting from sub-arachnoid haemorrhage, neural shock, cerebral ischaemia, Parkinson's Disease, migraine and/or psychosis, in mammals, especially humans.

In a yet further aspect the invention provides the use of a compound of formula (Ia), or a pharmaceutically acceptable salt thereof, for the manufacture of a medicament for the treatment and/or prophylaxis of anxiety, mania, depression, the effects associated with withdrawal from substances of abuse such as cocaine, nicotine, alcohol and benzodiazepines and/or disorders treatable or preventable with anti-convulsive agents, such as epilepsy.

Such compositions may be prepared in the manner as hereinbefore described.

The invention also provides novel compounds of formula (I) and (Ia) and pharmaceutically acceptable salts thereof. The present invention also extends to pharmaceutical compositions containing novel compounds admixed with a pharmaceutically acceptable carrier as well as to the use of such novel compounds as therapeutic agents, in particular to the use of the compounds in any of the utilities mentioned herein.

Novel compounds are:
trans-6-ethyl-3,4-dihydro-2,2-dimethyl-4S-(2-pyridinylcarbonyl)amino-2H-1-benzopyran-3R-ol,
trans-6-cyano-4S-(5-chloro-2-thiophenylcarbonylamino)-3,4-dihydro-2,2-dimethyl-2H-1-benzopyran-3R-ol,
trans-4-(4-chlorobenzoylamino)-6-cyano-3,4-dihydro-2,2-dimethyl-2H-1-benzopyran-3-ol,
trans-6-cyano-3,4-dihydro-2,2-dimethyl-4S-(4-nitrobenzoylamino)-2H-1-benzopyran-3R-ol,
trans-4S-(4-aminobenzoylamino)-6-cyano-3,4-dihydro-2,2-dimethyl-2H-1-benzopyran-3R-ol,
trans-6-cyano-4-(4-trifluoromethyl-benzoylamino)-3,4-dihydro-2,2-dimethyl-2H-1-benzopyran-3-ol,
trans-6-Cyano-4-(2-iodobenzoylamino)-3,4-dihydro-2,2-dimethyl-2H-1-benzopyran-3-ol,
tans-4-(3-Bromo-4-fluorobenzoylamino)-6-ethyl-3,4-dihydro-2,2-dimethyl-2H-1-benzopyran-3R-ol,
trans-4S-(3-Bromo-4-fluorobenzoylamino)-6-ethyl-3,4-dihydro-2,2-dimethyl-2H-1-benzopyran-3R-ol,
trans-6-Ethyl-4-(3-trifluoro-4-fluorobenzoylamino)-3,4-dihydro-2,2-dimethyl-2H-1-benzopyran-3-ol,
trans-4-(4-Bromobenzoylamino)-6-ethyl-3,4-dihydro-2,2-dimethyl-2H-1-benzopyran-3-ol,
trans-4-(3-Fluoro4-methylbenzoylamino)-6-ethyl-3,4-dihydro-2,2-dimethyl-2H-1-benzopyran-3-ol,
trans-4-(3-fluoro4-methoxyamino)-6-ethyl-3,4-dihydro-2,2-dimethyl-2H-1-benzopyran-3-ol,
tans-4-(3-Chloro-4-fluorobenzoylamino)-6-ethyl-3,4-dihydro-2,2-dimethyl-2H-1-benzopyran-3-ol,
trans-4-(3-bromobenzoylamino)-6-ethyl-3,4-dihydro-2,2-dimethyl-2H-1-benzopyran-3-ol,
trans4-(4-Fluoro-3-methylbenzoylamino)-6-ethyl-3,4-dihydro-2,2-dimethyl-2H-1-benzopyran-3-ol,
trans-6-Acetyl-4-(3-bromo-4-fluorobenzoylamino)-3,4-dihydro-2,2-dimethyl-2H-1-benzopyran-3-ol,
trans-6-Acetyl-4-(3-bromobenzoylamino)-3,4-dihydro-2,2-dimethyl-2H-1-benzopyran-3-ol,
trans-6-Acetyl-4-(2-bromobenzoylamino)-3,4-dihydro-2,2-dimethyl-2H-1-benzopyran-3-ol,
trans-6-Acetyl-4-(-bromo-2-furanoylamino)-3,4-dihydro-2,2-dimethyl-2H-1-benzopyran-3-ol,
trans-6-Acetyl-4-(2-azidobenzoylamino)-3,4-dihydro-2,2-dimethyl-2H-1-benzopyran-3-ol,
trans-6-Acetyl4-(3-azidobenzoylamino)-3,4-dihydro-2,2-dimethyl-2H-1-benzopyran-3-ol,
trans-6-Acetyl-4-(3-chlorobenzoylamino)-3,4-dihydro-2,2-dimethyl-2H-1-benzopyran-3-ol,
trans-6-Acetyl-4-(3-trifluoromethylbenzoylamino)-3,4-dihydro-2,2-dimethyl-2H-1-benzopyran-3-ol,
trans-6-Acetyl-4-benzoylamino-3,4-dihydro-2,2-dimethyl-2H-1-benzopyran-3-ol,
trans-6-Acetyl4-(2-iodobenzoylamino)-3,4-dihydro-2,2-dimethyl-2H-1-benzopyran-3-ol,
trans-6-Acetyl-4-(3-iodobenzoylamino)-3,4-dihydro-2,2-dimethyl-2H-1-benzopyran-3-ol,
trans-6-Acetyl-4-(2-nitrobenzoylamino)-3,4-dihydro-2,2-dimethyl-2H-1-benzopyran-3-ol,
trans-6-Acetyl-4-(2-chlorobenzoylamino)-3,4-dihydro-2,2-dimethyl-2H-1-benzopyran-3-ol,
trans-6-Acetyl-4-(3-cyanobenzoylamino)-3,4-dihydro-2,2-dimethyl-2H-1-benzopyran-3-ol,
trans-6-Acetyl-4-(4-chlorobenzoylamino)-3,4-dihydro-2,2-dimethyl-2H-1-benzopyran-3-ol,
trans-6-Acetyl4-(2-aminobenzoylamino)-3,4-dihydro-2,2-dimethyl-2H-1-benzopyran-3-ol,
trans-6-Acetyl-4-(3-nitrobenzoylamino)-3,4-dihydro-2,2-dimethyl-2H-1-benzopyran-3-ol,
trans-6-Acetyl-4-(2-trifluoromethoxybenzoylamino)-3,4-dihydro-2,2-dimethyl-2H-1-benzopyran-3-ol,
trans-6-Acetyl-4S-(2-chlorobenzoylamino)-3,4-dihydro-2,2-dimethyl-2H-1-benzopyran-3R-ol,
trans-6-Acetyl-4-(2,3-dichlorobenzoylamino)-3,4-dihydro-2,2-dimethyl-2H-1-benzopyran-3-ol,
trans-6-Acetyl-4-(2-chloro-4-fluorobenzoylamino)-3,4-dihydro-2,2-dimethyl-2H-1-benzopyran-3-ol, trans-6-Acetyl-4S-(2-chloro-4-fluorobenzoylamino)-3,4-dihydro-2,2-dimethyl-2H-1-benzopyran-3R-ol,
trans-6-Acetyl-4S-(2-trifluoromethylbenzoylamino)-3,4-dihydro-2,2-dimethyl-2H-1-benzopyran-3R-ol,
trans-6-Acetyl-4S-(3-chlorobenzoylamino)-3,4-dihydro-2,2-dimethyl-2H-1-benzopyran-3R-ol,
trans-6-Acetyl-4-(3-chlorothiophen-2-carbonylamino)-3,4-dihydro2,2-dimethyl-2H-1-benzopyran-3-ol,
trans-6-Acetyl-4S-(2-chlorothiophen-3-carbonylamino)-3,4-dihydro-2,2-dimethyl-2H-1-benzopyran-3R-ol,
trans-6-Acetyl-4-(5-bromothiophen-2-carbonylamino)-3,4-dihydro-2,2-dimethyl-2H-1-benzopyran-3-ol,
trans-6-Acetyl-4-(3,5-dibromobenzoylamino)-3,4-dihydro-2,2-dimethyl-2H-1-benzopyran-3-ol,
trans-6-Acetyl-4-(2-chloro-6-fluorobenzoylamino)-3,4-dihydro-2,2-dimethyl-2H-1-benzopyran-3-ol,
trans-6-Acetyl-4-(3-chloro-2-fluorobenzoylamino)-3,4-dihydro-2,2-dimethyl-2H-1-benzopyran-3-ol,
trans-6-Acetyl-4-(2,6-dichlorobenzoylamino)-3,4 dihydro-2,2-dimethyl-2H-1-benzopyran-3-ol,
trans-6-Acetyl-4-(2-azido4-fluorobenzoylamino)-3,4-dihydro-2,2-dimethyl-2H-1-benzopyran-3-ol,
trans-6-Acetyl-4-(2-azido-5-fluorobenzoylamino)-3,4-dihydro-2,2-dimethyl-2H-1-benzopyran-3-ol,
trans-6-Acetyl4S-(2-methylbenzoylamino)-3,4-dihydro-2,2-dimethyl-2H-1-benzopyran-3R-ol,
trans-6-Acetyl-4S-(4-methylbenzoylamino)-3,4-dihydro-2,2-dimethyl-2H-1-benzopyran-3R-ol,
trans-6-Acetyl-4-(2-chloro-3-nitrobenzoylamino)-3,4-dihydro-2,2-dimethyl-2H-1-benzopyran-3-ol,
trans-6-Acetyl-4-(2-chloro-5-nitrobenzoylamino)-3,4-dihydro-2,2-dimethyl-2H-1-benzopyran-3-ol,
trans-6-Acetyl4-(2-methoxybenzoylamino)-3,4-dihydro-2,2-dimethyl-2H-1-benzopyran-3-ol,
trans-6-Acetyl-4S-(3-chloro-4-fluorobenzoylamino)-3,4-dihydro-2,2-dimethyl-2H-1-benzopyran-3R-ol,
trans-6-Acetyl-4-(2-chloro-4-hydroxybenzoylamino)-3,4-dihydro-2,2-dimethyl-2H-1-benzopyran-3-ol.

Generally, compounds of formula (I) and (Ia) may be prepared by procedures generally described or analogous to those described in EP-0126311, EP-0376524, EP-205292, EP-0250077, EP-0093535, EP-0150202, EP-0076075, WO/89/05808, EP-0350805, EP-0277611, EP-0277612, EP-0337179, EP-0355565, EP-A-415 065, EP-A-450 415, EP-A-0482934, EP-A-0296975, JO-2004-791 and WO\89\07103 EP-0466131.

The invention also provides a process for the preparation of a compound of formula (Ia) or pharmaceutically acceptable salts thereof existing predominantly in the 4S, 3R form, which comprises acylating a compound of formula (II):

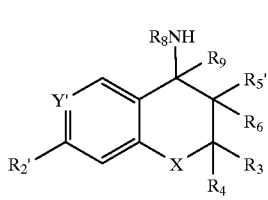

(II)

wherein Y', $R_2$' and $R_5$' are the required variables Y, $R_2$ or $R_5$ as defined in formula (Ia) or a group convertible thereto and $R_3$, $R_4$, $R_6$, $R_8$, $R_9$ and X are the required variables as defined in formula (Ia), the $R_8$NH group being trans to the $R_5$ group; with an acylating agent of formula (III):

$R_7COL_1$ (III)

where $R_7$ is as required and as defined in formula (Ia) and $L_1$ is a leaving group; thereafter optionally or as necessary and in any appropriate order converting any $R_1$', $R_2$' and $R_5$' groups to $R_1$, $R_2$ and $R_5$ respectively, interconverting $R_8$ when hydrogen to $C_{1-6}$ alkyl, separating any enantiomers, and forming a pharmaceutically acceptable salt.

Examples of suitable leaving groups $L_1$ include those mentioned in the above-mentioned patents, in particular EP-A-0 126 311 or are conventional in the art.

The reaction conditions which may be used to carry out the above reactions are as outlined or analogous to those described in the above-mentioned patents, in particular EP-A-0 126 311.

In particular, the leaving group ($L_1$) is a group that is displaceable by a primary or secondary amino nucleophile. Examples of such a group include $C_{1-4}$ alkylcarbonyloxy and halogen, such as chloro and bromo. When the leaving group ($L_1$) is any of these examples, the acylating agent of formula (III) is either an acid anhydride or an acid halide. When it is an acid anhydride, it is, preferably, a mixed anhydride, which may be prepared in situ from an aromatic or heteroaromatic carboxylic acid and an alkyl chlorocarbonate, such as ethyl chloroformate.

When the acylating agent of formula (III) is an acid anhydride, the acylation of the compound formula (II), is, preferably carried out using the anhydride as the solvent in the presence of an acid acceptor, such as sodium acetate.

When the acylating agent of formula (III) is an acid halide, the acylation of the compound of formula (II), is, preferably. carried out in a non-aqueous medium, such as methylene chloride, in the presence of an acid acceptor, such as triethylamine, trimethylamine or pyridine.

Examples of suitable groups convertible to Y (or $R_1$), $R_2$ and $R_5$ include those described in the above-mentioned patents or are conventional in the art.

Interconversions of $R_8$ when hydrogen to $C_{1-6}$ alkyl may be carried out using conventional alkylation procedures for example using an alkylhalide in the presence of a base.

It should be appreciated that racemates for formula (I) and (Ia) may be resolved or enantiomerically purified compounds of formula (I) may be prepared using procedures conventional in the art and in particular using the procedures outlined in EP-0430631 and EP-0355584.

It should be appreciated that it is preferred that the compounds of formula (I) and (Ia) may be prepared in the required enantiomeric form by forming a chirally pure epoxide precursor to compounds of formula (II) using catalysts and conditions generally outlined in the WO 91\14694 or WO 91\17026 and thereafter converted to the required compound using procedures outlined hereinbefore.

Compounds of formulae (III) are either commercially available or may be prepared according to conventional procedures known in the art of organic chemistry.

Compounds of formula (I) in which $R_5$ is hydroxy, $R_6$ is $C_{1-2}$ alkyl and $R_9$ is hydrogen may be prepared according to the procedures outlined in R. Gericke et al. J. Med. Chem. Vol.34, p3074(1991).

The following compounds were prepared as described or by using by methods analgous to those described in the abovementioned patents publications.

The following examples and pharmacological test results illustrate the present invention:

EXAMPLE 1 trans-6-cyano-3,4-dihydro-2,2-dimethyl-4-(2-pyridinylcarbonyl)amino-2H-1-benzopyran-3-ol This compound was prepared exactly as described in European patent specification 126 311 with mp 165° C., from ethyl acetate-pentane.

EXAMPLE 2
trans6-ethyl-3,4-dihydro-2,2-dimethyl4S-(2-pyridinylcarbonyl)amino-2H-1-benzopyran-3R-ol To a solution of picolinic acid (0.66 g), 1-hydroxybenzotriazole (0.724 g) and 1-(3-dimethylaminopropyl)-3-ethylcarbodiimide hydrochloride (1.03 g) in dimethyl formamide (20 mL), stirred for 20 minutes, was added trans-4S-amino-3,4-dihydro-2,2-dimethyl-2H-1-benzopyran-3R-ol D-(−)-mandelate salt (2.0 g) and triethylamine (0.542 g). The solution was allowed to stir for a further 16 hours. The solvent was evaporated and the residue taken up into ethyl acetate and washed with dilute HCl, water, 5% sodium bicarbonate solution, and brine, before drying over anhydrous magnesium sulphate. Filtration and evaporation, and recrystallisation from ethyl acetate-hexane gave the compound of example 2 as crystals of mp 94–95°C.

NMR (DMSO-$d_6$) d 1.03 (3H, t), 1.14 (3H, s), 1.36 (3H, s), 2.43 (2H, q), 3.85 (1H,q), 5.02 (1H, t), 5.47 (1H, d), 6.67 (1H, d), 6.86 (1H, br s), 6.97 (1H, q), 7.63 (1H, m), 8.03 (1H, m), 8.14 (1H, m), 8.64 (1H, m), 8.96 (1H, d). $[\alpha]_D^{25}$ +81.0°, MeOH (c=1.0)

EXAMPLE 3
trans-6-cyano-4-(2-furoylamino)-3,4-dihydro-2,2-dimethyl-2H-1-benzopyran-3-ol The compound of this example was prepared exactly as described in European patent specification 126 311.

EXAMPLE 4
trans-6-cyano-4-(3-furoylamino)-3,4-dihydro-2,2-dimethyl-2H-1-benzopyran-3-ol The compound of this example was prepared exactly as described in European patent specification 126 311.

EXAMPLE 5
trans-6-cyano-4S-(5-chloro-2-thiophenylcarbonyiamino)-3,4-dihydro-2,2-dimethyl-2H-1-benzopyran-3R-ol To a stirred ice cooled solution of 5-chloro-2-thiophene carboxylic acid (1.625 g, prepared by carbonylation of lithiated 2-chlorothiophene), 1-hydroxybenzotriazole (1.35 g) and 1-(3-dimethylaminopropyl)-3-ethylcarbodiimide hydrochloride (1.92 g) in dimethylformamide (60 mL) and triethylamine (1.01 g), was added tans-4S-amino-6-cyano-3,dihydro-2,2-dimethyl-2H-1-benzopyran-3R-ol (2.535 g). The reaction mixture was allowed to attain room temperature, and stirred for an additional 72 hours. The solvent was evaporated, and the residue taken up into ethyl acetate, and the organic phase washed with 1N HCl, water, saturated sodium bicarbonate solution and dried over anhydrous magnesium sulphate. Filtration and evaporation gave a solid (3.3 g) which was recrystallised from ethyl acetate—60–80° petroleum ether as crystals of mp 234–236° C.; $[a]_D^{20}$+53.4° (MeOH, c=1).

EXAMPLE 6
trans-4-(4-chlorobenzoylamino)-6-cyano-3,4-dihydro-2,2-dimethyl-2H-1-benzopyran-3-ol To a stirred solution of trans-4-amino-6cyano-3,4-dihydro-2,2-dimethyl-2H-1-benzopyran-3-ol (1.0 g), triethylamine (0.64 mL) and dichloromethane was added 4-chlorobenzoyl chloride (0.55 mL). The solution was stirred for a further 1.5 hours. The solution was washed with water and brine and dried over anhydrous magnesium sulphate. The solution was filtered and evaporated and recrystallised from ethyl acetate—60–80° petroleum ether as a white solid of mp 226–229° C.

EXAMPLE 7
trans-6-cyano-3,4-dihydro-2,2-dimethyl-4S-(4-nitrobenzoylamino)-2H 1-benzopyran-3R-ol This compound was prepared as the hemihydrate as described in example 9 using 4-nitrobenzoyl chloride as the acylating agent. When the reaction mixture was washed with water, the compound of example 7 precipitated out, and was collected by filtration. The solid product had mp 288–294° C.

EXAMPLE 8
trans4S-(4-aminobenzoylamino)-6-cyano-3,4-dihydro-2,2-dimethyl-2H-1-benzopyran-3R-ol The compound of example 7 (450 mg) and tin (II) chloride (470 mg) were heated under gentle reflux for 1 hour in an atmosphere of nitrogen. A further 380 mg of the tin reagent was added, and the reaction continued for a further 2 hours. The solution was cooled and poured into ice-water and extracted with chloroform, and dried over anhydrous sodium sulphate. Filtration and evaporation and column chromatography gave the compound of example 8 as solid of mp 279–283° C.

EXAMPLE 9
trans-6-cyano-4-(4-trifluoromethyl-benzoylamino)-3,4-dihydro-2,2-dimethyl-2H-1-benzopyran-3-ol.

The compound of example 9 was prepared as described for example 6, using 4-trifluoromethyl-benzoyl chloride as the acylating agent. The crude product was recrystallised from ethyl acetate as crystals of mp 225° C.

EXAMPLE 10
trans-6-Cyano-4-benzoylamino-3,4-dihydro-2,2-dimethyl-2H-1-benzopyran-3-ol.
mp 192.5–194° C.;
[already published as example 1 and method for prep in EP 126 311 and in Ashwood t al., J Med Chem 33, 2667–2672 (1990)]

EXAMPLE 11
trans-6-Cyano-4-(4-cyanobenzoylamino)-3,4-dihydro-2,2-dimethyl-2H-1-benzopyran-3-ol.
mp 260–262° C.; [example 2 in EP 126 311]

EXAMPLE 12
trans-6-Cyano-4-(3-nitrobenzoylamino)-3,4-dihydro-2,2-dimethyl-2H-1-benzopyran-3-ol.
mp 218–220° C.; [example 3 in EP 126 311]

EXAMPLE 13
trans-4-(3,4-Dichlorobenzoylamino)-6-cyano-3,4-dihydro-2,2-dimethyl-2H-1-benzopyran-3-ol.
mp 230–231° C.; [example 4 in EP 126311]

EXAMPLE 14
trans-6-Cyano-4-(2-iodobenzoylamino)-3,4-dihydro-2,2-dimethyl-2H-1-benzopyran-3-ol.
mp 189–192° C.

EXAMPLE 15
trans-4-(3-Bromo-4-fluorobenzoylamino)-6-ethyl-3,4-dihydro-2,2-dimethyl-2H-1-benzopyran-3-ol.
mp 122° C.

EXAMPLE 16
trans-4S-(3-Bromo-4-fluorobenzoylamino)-6-ethyl-3,4-dihydro-2,2-dimethyl-2H-1-benzopyran-3R-ol.
mp 70° C.; $[\alpha]_D^{25}$ +54.5°, MeOH (c=1.0)

EXAMPLE 17
trans-6-Ethyl-4-(3-trifluoro-4-fluorobenzoylamino)-3,4-dihydro-2,2-dimethyl-2H-1-benzopyran-3-ol.
mp 177° C.

EXAMPLE 18
trans-4-(4-Bromobenzoylamino)-6-ethyl-3,4-dihydro-2,2-dimethyl-2H-1-benzopyran-3-ol.
mp 190–191° C.

EXAMPLE 19
trans-4-(3-Fluoro-4-methylbenzoylamino)-6-ethyl-3,4-dihydro-2,2-dimethyl-2H-1-benzopyran-3-ol.
mp 166° C.

EXAMPLE 20
trans-4-(3-fluoro-4-methoxyamino)-6-ethyl-3,4-dihydro-2,2-dimethyl-2H-1-benzopyran-3-ol.
mp 178° C.

EXAMPLE 21
trans-4-(3-Chloro-4-fluorobenzoylamino)-6-ethyl-3,4-dihydro-2,2-dimethyl-2H-1-benzopyran-3-ol.
mp 146° C.

EXAMPLE 22
trans4-(3-bromobenzoylamino)-6-ethyl-3,4-dihydro-2,2-dimethyl-2H-1-benzopyran-3-ol.
mp 151° C.

EXAMPLE 23
trans-4-(4-Fluoro-3-methylbenzoyiamino)-6-ethyl-3,4-dihydro-2,2-dimethyl-2H-1-benzopyran-3-ol.
mp 103° C.

EXAMPLE 24
trans-6-Acetyl-4-(3-bromo-4-fluorobenzoylamino)-3,4-dihydro-2,2-dimethyl-2H-1-benzopyran-3-ol.
mp 181° C.

EXAMPLE 25
trans-6-Acetyl-4-(3-bromobenzoylamino)-3,4-dihydro-2,2-dimethyl-2H-1-benzopyran-3-ol.
mp 206° C.

EXAMPLE 26
trans-6-Acetyl-4-(2-bromobenzoylamino)-3,4-dihydro-2,2-dimethyl-2H-1-benzopyran-3-ol.
mp 212° C.

EXAMPLE 27
trans-6-Acetyl-4-(5-bromo-2-furanoylamino)-3,4-dihydro-2,2-dimethyl-2H-1-benzopyran-3-ol.
mp 185° C.

EXAMPLE 28
trans-6-Acetyl-4-(2-azidobenzoylamino)-3,4-di hydro-2,2-dimethyl-2H-1-benzopyran-3-ol.
mp 177–179° C.

EXAMPLE 29
trans-6-Acetyl-4-(3-azidobenzoylamino)-3,4-dihydro-2,2-dimethyl-2H-1-benzopyran-3-ol.
mp 181–183° C.

EXAMPLE 30
trans-6-Acetyl-4-(3-chlorobenzoylamino)-3,4-dihydro-2,2-dimethyl-2H-1-benzopyran-3-ol.
mp 180° C.

EXAMPLE 31
trans-6-Acetyl-4-(3-trifluoromethylbenzoylamino)-3,4-dihydro-2,2-dimethyl-2H-1-benzopyran-3-ol.
mp 206° C.

EXAMPLE 32
trans-6-Acetyl-4-benzoylamino-3,4-dihydro-2,2-dimethyl-2H-1-benzopyran-3-ol.
mp 217° C.

EXAMPLE 33
trans-6-Acetyl-4-(2-iodobenzoylamino)-3,4-dihydro-2,2-dimethyl-2H 1-benzopyran-3-ol.
mp 239° C.

EXAMPLE 34
trans-6-Acetyl-4-(3-iodobenzoylamino)-3,4-dihydro-2,2-dimethyl-2H-1-benzopyran-3-ol.
mp 215° C.

EXAMPLE 35
trans-6-Acetyl-4-(2-nitrobenzoylamino)-3,4-dihydro-2,2-dimethyl-2H-1-benzopyran-3-ol.
mp 251° C.

EXAMPLE 36
trans-6-Acetyl-4-(2-chlorobenzoylamino)-3,4-dihydro-2,2-dimethyl-2H-1-benzopyran-3-ol.
mp 207° C.

EXAMPLE 37
trans-6-Acetyl-4-(3-cyanobenzoylamino)-3,4-dihydro-2,2-dimethyl-2H-1-benzopyran-3-ol.
mp 184° C.

EXAMPLE 38
trans-6-Acetyl-4-(4-chlorobenzoylamino)-3,4-dihydro-2,2-dimethyl-2H-1-benzopyran-3-ol.
mp 215° C.

EXAMPLE 39
trans-6-Acetyl-4-(2-aminobenzoylamino)-3,4-dihydro-2,2-dimethyl-2H-1-benzopyran-3-ol.
mp 193° C.

EXAMPLE 40
trans-6-Acetyl-4-(3-nitrobenzoylamino)-3,4-dihydro-2,2-dimethyl-2H-1-benzopyran-3-ol.
mp 243° C.

EXAMPLE 41
trans-6-Acetyl-4-(2-trifluoromethoxybenzoylamino)-3,4-dihydro-2,2-dimethyl-2H-1-benzopyran-3-ol.
mp 201° C.

EXAMPLE 42
trans-6-Acetyl-4S-(2-chlorobenzoylamino)-3,4-dihydro-2,2-dimethyl-2H-1-benzopyran-3R-ol.
mp 195° C.; $[a]_D^{25}$ +6.8°, MeOH (c=1.0); NMR (DMSO$_{d-6}$) δ 1.32 (s, 3H), 1.53 (s, 3H), 2.57 (s, 3H), 3.77 (q, J=10, 6 Hz, 1H), 5.14 (t, J=10, 10 Hz, 1H), 5.88 (d J=6 Hz, 1H), 6.97 (d, J=8 Hz), 7.50–7.72 (m, 4H), 7.88 (q, J=8, 2 Hz, 1H), 8.09 (d, J=2 Hz, 1H), 8.95 (d, J=10 Hz, 1H).

EXAMPLE 43
trans-6-Acetyl-4-(2,3-dichlorobenzoylamino)-3,4-dihydro-2,2-dimethyl-2H-1-benzopyran-3-ol.
mp 213–215° C.

EXAMPLE 44
trans-6-Acetyl-4-(2-chloro-4-fluorobenzoyiamino)-3,4-dihydro-2,2-dimethyl-2H-1-benzopyran-3-ol.
mp 196° C.

EXAMPLE 45
trans-6-Acetyl-4S-(2-chloro-4-fluorobenzoylamino)-3,4-dihydro-2,2-dimethyl-2H-1-benzopyran-3R-ol.
mp 204° C.; NMR (DMSO$_{d-6}$) δ 1.23 (s, 3H), 1.46 (s, 3H), 2.48 (s, 3H), 3.66 (d, J=9, 6 Hz, 1H), 5.02 (t, J=9, 9 Hz, 1H), 5.85 (d, J=6 Hz, 1H), 6.88 (d, J=8 Hz, 1H), 7.37 (m, 1H), 7.57 (m, 1H), 7.67 (m, 1H), 7.79 (q, J=8, 2 Hz, 1H), 7.97 (nartow m, 1H), 8.91 (d, J=9 Hz, 1H). [a]$_D^{25}$ +10.0°, MeOH (c=0.97)

EXAMPLE 46
trans-6-Acetyl-4S-(2-trifluoromethylbenzoylamino)-3,4-dihydro-2,2-dimethyl-2H-1-benzopyran-3R-ol.
mp 219–221° C.

EXAMPLE 47
trans-6-Acetyl-4S-(3-chlorobenzoylamino)-3,4-dihydro-2,2-dimethyl-2H-1-benzopyran-3R-ol.
mp 168° C.; [α]$_D^{25}$ +21.9°, MeOH (c=1.01)

EXAMPLE 48
trans-6-Acetyl-4-(3-chlorothiophen-2-carbonylamino)-3,4-dihydro-2,2-dimethyl-2H-1-benzopyran-3-ol.
mp 173° C.

EXAMPLE 49
trans-6-Acetyl-4S-(2-chlorothiophen-3-carbonylamino)-3,4-dihydro-2,2-dimethyl-2H-1-benzopyran-3R-ol.

EXAMPLE 50
trans-6-Acetyl-4-(5-bromothiophen-2-carbonylamino)-3,4-dihydro-2,2-dimethyl-2H-1-benzopyran-3-ol.
mp 186° C.

EXAMPLE 51
trans-6-Acetyl-4-(3,5-dibromobenzoylamino)-3,4-dihydro-2,2-dimethyl-2H-1-benzopyran-3-ol.
mp 262° C.

EXAMPLE 52
trans-6-Acetyl-4-(2-chloro-6-fluorobenzoylamino)-3,4-dihydro-2,2-dimethyl-2H-1-benzopyran-3-ol.
mp 193° C.

EXAMPLE 53
trans-6-Acetyl-4-(3-chloro-2-fluorobenzoylamino)-3,4-dihydro-2,2-dimethyl-2H-1-benzopyran-3-ol.
mp 190° C.

EXAMPLE 54
trans-6-Acetyl-4-(2,6-dichlorobenzoylamino)-3,4-dihydro-2,2-dimethyl-2H-1-benzopyran-3-ol.
mp 187–188° C.

EXAMPLE 55
trans-6-Acetyl-4-(2-azido-4-fluorobenzoylamino)-3,4-dihydro-2,2-dimethyl-2H-1-benzopyran-3-ol.
mp 181–183° C.

EXAMPLE 56
trans-6-Acetyl-4-(2-azido-5-fluorobenzoylamino)-3,4-dihydro-2,2-dimethyl-2H-1-benzopyran-3-ol.
mp 166–168° C.

EXAMPLE 57
trans6-Acetyl-4S-(2-methylbenzoylamino)-3,4-dihydro-2,2-dimethyl-2H-1-benzopyran-3R-ol.
mp 198–200° C.

EXAMPLE 58
trans-6-Acetyl-4S-(4-methylbenzoylamino)-3,4-dihydro-2,2-dimethyl-2H-1-benzopyran-3R-ol.

EXAMPLE 59
trans-6-Acetyl-4-(2-chloro-3-nitrobenzoylamino)-3,4-dihydro-2,2-dimethyl-2H-1-benzopyran-3-ol.
mp 221° C.

EXAMPLE 60
trans-6-Acetyl-4-(2-chloro-5-nitrobenzoylamino)-3,4-dihydro-2,2-dimethyl-2H-1-benzopyran-3-ol.
mp 216–217° C.

EXAMPLE 61
trans-6-Acetyl-4-(2-methoxybenzoylamino)-3,4-dihydro-2,2-dimethyl-2H-1-benzopyran-3-ol.
mp 149° C.

EXAMPLE 62
trans-6-Acetyl-4S-(3-chloro-4-fluorobenzoylamino)-3,4-dihydro-2,2-dimethyl-2H-1-benzopyran-3R-ol.
mp 110° C.

EXAMPLE 63
trans-6-Acetyl-4-(2-chloro-4-hydroxybenzoylamino)-3,4-dihydro-2,2-dimethyl-2H-1-benzopyran-3-ol.

EXAMPLE 64
trans-4-(4-fluorobenzoylamino)-3,4-dihydro-2,2-dimethyl-6-nitro-2H-1-benzopyran-3-ol.
mp 197–198° C.

EXAMPLE 65
trans-6-Acetyl-4-(4-methylbenzoylamino)-3,4-dihydro-2,2-dimethyl-2H-1-benzopyran-3-ol.
mp 255–2560° C.

EXAMPLE 66
trans-6-cyano-4R-(3-fluorobenzoylamino)-3,4-dihydro-2,2-dimethyl-2H-1-benzopyran-3S-ol.
As in Example 22 of PCT/GB92/01045.

EXAMPLE 67
trans-6-Acetyl-4S-(213-dichlorobenzoylamino)-3,4-dihydro-2,2-dimethyl-2H-1-benzopyran-3R-ol.
Nmr—(CDCl$_3$) 31.35 (s, 3H), 1.55 (s, 3H), 2.55(s, 3H), 3.80 (d, 1H), 5.33 (t, 1H), 6.55 (d, 1H), 6.90 (d, 1H), 7.28–7.42 (m, 1H), 7.52–7.70 (m, 2H), 7.82 (m, 1H), 8.06 (5,1H)

EXAMPLE 68
trans-6-Acetyl-3,4-dihydro-2,2-dimethyl-4-(2-pyrazinecarboxybenzoyiamino)-2H-1-benzopyran-3-ol.
mpt 265–267° C.

PHARMACOLOGICAL DATA

1. Rat Social Interaction Test

The compounds of formula (I) or pharmaceutically acceptable salts thereof are tested for therapeutic utility using the procedure outlined as follows:

Potential anxiolytic properties are evaluated using the rat social interaction procedure based on that originally described by File (1980, J. Neurosci. Methods, 2, 219–238). In this model anxiolytic agents selectively increase social interaction independently of any effect on locomotor activity.

Method

Male Sprague-Dawley rats (Charles River, U.K., 250–300 g) are singly housed for 3 days prior to testing. On the test day, the animals are then randomly assigned to groups of 8–16 and dosed orally at a dose volume of 1 ml/kg with various doses of compound (1–300 mg/kg) or vehicle. At 60 min post dose the rats are placed with a weight-and treatment-matched pair male (encountered for the first time) in the social interaction box under high-light, unfamiliar conditions. The box is made of white perspex 54×37×26 cm with a transparent perspex front side. The floor is divided into 24 equal squares and is brightly lit (115 lux). Time spent (secs) in active social interaction (sniffing, grooming, following, mounting, climbing over or under, boxing, biting) is scored "blind" by remote monitoring as is the number of squares crossed (as an index of locomotion).

The mean and standard error for time spent in social interaction and number of squares crossed are then calculated for each particular treatment group and drug-induced changes are expressed as a percentage increase or decrease from control values. Statistical comparisons are made between vehicle- and drug-treated groups using Dunnett's multiple comparisons procedure following significant one way analysis of varience.

Drugs are suspended in 1% methyl cellulose.

2. MES TEST

The maximal electroshock seizure (MES) threshold test in rodents is particularly sensitive for detecting potential anticonvulsant properties[1]. In this model, anticonvulsant agents elevate the threshold to electrically-induced seizures whilst proconvulsants lower the seizure threshold.

Method

The compounds of formula (I) or pharmaceutically acceptable salts thereof are tested for therapeutic utility using the procedures outlined as follows:

Mice (male, Charles River, U.K. CD-1 strain, 25–30g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Stastical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

The percentage increase or decrease in $CC_{50}$ for each group compared to the control is calculated.

Studies are carried out using a Hugo Sachs Electronik Constant Current Shock Generator with totally variable control of shock level from 0 to 300 mA and steps of 2 mA are usually used.

Drugs are suspended in 1% methyl cellulose.

References

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther. 96, 99–113

Results

The compound of example 2 enhanced seizure threshold by 44% at 30 mg/kg p.o.

The compund of example 42 enhanced seizure threshold by 129% at 30 mg/kg p.o.

The compound of example 44 enhanced seizure threshold by 154% at 30 mg/kg p.o.

3. X-Maze

Introduction

The compounds of formula (I) or pharmaceutically acceptable salts thereof are tested for therapeutic utility using the procedures outlined as follows:

The X-maze test of anxiety (Handley and Mithani, 1984) examines the exploratory response of naive rats in an environment which offers both anxiogenic (open arms) and relatively non-anxiogenic (closed arms) areas. A selective increase in exploration of the open arms following drug pretreatment is therefore postulated to indicate anxiolytic effects.

Method

The X-maze was raised 70 cm above the floor and consisted of two enclosed arms 45 cm (long)×15 cm (wide)× 10 cm (high) and two open arms 45×10×1 cm arranged such that the two arms of each type were opposite each other. Both arm types were marked into two equal sections. Rats were placed onto the centre of the X-maze and observed for a period of 10 minutes during which time the following parameters were recorded: 1) the number of entries onto, and the time spent on, (a) open arms, (b) closed arms, (c) end of open arms and (d) end of closed arms. 2) the number of sections crossed. The fear-drive evoked in the open arms exceeds that in the enclosed arms and rats typically show a clear preference for the enclosed arms. Anxiolytic drugs increase the number of entries made onto, and the time spent on, the outer half of the open arms, and also the percentage of entries made onto, and the time spent on, the whole of the open arms. These four measures of anxiety, and also the total number of sections traversed, were calculated for each animal. Drugs are administered intraperitoneally or orally to groups of 6 to 12 rats 30 to 60 mins before testing. Statistical comparisons between vehicle-and drug-treated groups were made using a Mann-Whitney 'U' test (two tailed). S. L. Handley and S. Mithani, Arch. Pharmacol., 1984 327 1–5

4. Mongrel Dog Delayed Cerebral Vasospasm

Twenty-five male mongrel dogs, weighing 9–12 kg, are used in these studies. The animals are housed and cared for in accordance with the Guide for the Care and Use of Laboratory Animals [DHEW (DHHS) publication No. (NIH) 85–23 revised 1985]. All procedures using laboratory animals are approved by the Institutional Animal Care and Use Committee of SmithKline Beecham Pharmaceutical. Each animal is anaesthetized with pentobarbital (35 mg/kg, iv) and placed on a heated operating table in the supine position. All animals are then tracheotomized, paralyzed (tubocurarine; 0.1 mg/kg, i.v.) and artificially ventilated with room air. End-tidal $CO_2$ (et $CO_2$) is monitored continuously and arterial blood gas analysis was performed periodically to assure stable and adequate ventilation throughout each experiment. Polyethylene cannulae are placed in the left external jugular vein and the right femoral artery and vein for drug administration, monitoring arterial blood pressure, and blood sampling, respectively. Transfemoral catheterization of the left vertebral artery is then performed via the left femoral artery using a 5 french Lehman dacron catheter (Bard, Tewksbury Mass.). Anaesthesia is supplemented as needed with pentobarbital (5 mg/kg, i.v.) prior to the experimental period.

The effects of the compounds of this invention on acute cerebral vasospasm are evaluated in 15 dogs. In all animals a control digital subtraction angiogram of the anterior spinal artery and basilar artery is obtained following the intravertebral injection of radiocontrast material (Omnipaque 300). In each dog, 4 mls of cerebrospinal fluid is then removed from the dorsal cistern via needle puncture of the atlantooccipital membrane and 4 mls of autologous venous blood was injected. An angiogram is then repeated in each dog 30 minutes following the intracisternal administration of blood and an acute vasospasm of the basilar and anterior spinal arteries is identified and quantitated. The infusion of vehicle (10% polyethylene glycol 200) for 30 minutes has no effect on the acute vasospasm. The effect of a 30 minute infusion of test compounds on the reversal of acute vasospasm is observed in the basilar and anterior spinal arteries.

The effects of the compounds of this invention are also examined in the chronic canine model of delayed cerebral vasospasm (two haemorrhage model of cerebral vasospasm). In this model, a control vertebral angiogram is obtained and autologous blood is administered intracisternally on day 1 (as above). On day 3 the intracisternal administration of blood is repeated and the severe delayed vasospasm is quantitated angiographically on day 7 in all animals. The infusion of vehicle (10% polyethylene glycol 200) for 60 minutes has no effect on the delayed vasospasm observed in the basilar and anterior spinal arteries (n=5). The effect of an infusion of test compounds on the reversal of significantly delayed cerebral vasospasm is observed.

The compounds of formula (I) or pharmaceutically acceptable salts thereof are tested for therapeutic utility using the procedures outlined as follows:

5. The compounds of formula (I) or pharmaceutically acceptable salts thereof are tested for therapeutic utility using the procedures outlined as follows:

1) Anti-Parkinsonian Activity 6-Hydroxydopamine-lesioned rat model

The above test as described by Ungerstedt, U, 1971, Acta Physiol. Scand 367, 49–68, and/or Ungerstedt, U, 1971, Acta Physiol Scand. 69–93, may be used to determine the anti-Parkinsonian activity of compounds of formula(I) or pharmaceutically acceptable salts thereof.

2) Anti-Psychotic Activity Amphetamine-induced rat hyperlocomotion model

The above test as described by Kokkindis L, and Anisman, M, 1980, Psychological Bulletin, 88, 551–579, may be used to determine the anti-psychotic activity of compounds of formula (I) or pharmaceutically acceptable salts thereof.

3) Anti-Migraine Activity Cortical Spreading Depression and Migraine

The above test as described by Wahl et al, 1987, Brain Research, 411, 72–80 may be used to determine the anti-migraine activity of compounds of formula (I) or pharmaceutically acceptable salts thereof.

6. Cerebral ischaemia a) Mongolian Gerbil Test

The in vivo experiments were carried out on adult Mongolian gerbils (Tumblebrook Farm (Mass.). weighing 60–80 g. Transient forebrain ischemia was produced by bilateral carotid artery ligation under 2.5% isoflourane in 100% $O_2$ anesthesia, the animals being placed onto a heating pad to maintain body temperature at 37° C. The common carotid arteries were exposed and aneurism clips were placed on both arteries for a certain period of time indicated in the figure legends. PBN dissolved in saline was administered intraperitoneally as a bolus 30 min before occlusion (pretreatments) or immediately after and again at 6 h of reperfusion, followed by the same dose b.i.d. for 2 days (post-treatment). For quantification of CA1 neurons, animals were sacrificed at 7 days postischemia and perfused with buffered formalin.

Brains were removed, stored in formalin for 3 days, embedded in paraffin, cut at 7-$\mu$m-thick coronal sections (1.5–1.9 mm posterior to bregmal[15]) and stained with thionin. The number of intact neurons over a 750-$\mu$m length of the CA1 layer on both hippocampal sides of 3 sections was counted for each animal.

b) MCAO method

Three strains of mature male rts SHR were obtained from commercial vendors (Taconic Farms, Germantown, N.Y.; Charles River, Danvers, Mass.; and Charles River, respectively) at 18 wk of age (250–300 g in weight) and were housed for 2 to 4 weeks prior to utilization in these studies. In order to verify that the strains of animals studied were indeed hypertensive and normotensive, groups of animals from each strain were anesthetized with 2% isoflourane (Anaquest, Madison, Wis.) and chronically prepared under aseptic conditions for recording of blood pressure. The femoral artery was cannulated with polyethylene tubing (PE60; Clay Adams. Parsippany, N.J.) extending just into the descending aorta. The tubing was lead subdermally from the artery and exteriorized between the scapula just below the back of the neck and cleared/filled with sterile isotonic saline. Incisions were closed using 2–0 silk suture and treated with 5% lidocaine ointment (Astra Pharmaceuticals, Westborough, Mass.) Animals recovered from surgery/anesthesia within 5 min. Mean arterial blook pressures were recorded 4 to 5 h after surgery for 5 min/rat by connecting the exteriorized tubing in each rat to a Statham pressure transducer (P2.3 Db; Statham Medical Instruments. Los Angeles, Calif.) with output to a polygraph (Model R711: Beckman Instruments, Inc., Fullerton, Calif.).

Focal Stroke Procedure

MCAO or sham surgery was carried out in the SHR, SD rats under 35 sodium pentobarbital (65 mg/kg, i.p. and supplemented as needed) anesthesia. All animals were allowed free access to food and water prior to and after surgery. Body temperature was maintained at 37° C. using a heating pad throughout the surgical procedure. Surgery was conducted similar to that described previously (2.4). The right dorsal surface to the head and shaved and prepped with providone-iodine. and the rat placed in a stereotaxic device (David Kopf Instruments, Tujunga, Calif.) with the surgery (right) side of the head superior. A 1–2 cm incision was made between the orbit and the external auditory canal. The temporal muscle was dissected from the skull and retracted without damaging the zygomatic bond or mandibular nerve. Under an operating microscope and with saline irrigation, a 2–3 mm craniotomy was made just rostral to the zygomatic-squamosal skull suture. The dura was opened over the artery using the modified tip of a 30-gauge needle. For permanent right MCAO, using electrocoagulation (Force 2 Electrosurgical Generator, Valley Lab Inc., Boulder, Colo.), the artery was stimultaneously occluded and cut dorsal to the lateral olfactory tract at the level of the inferior cerebral vain. A small piece of sterile saline-soaked Gelfoam (Upjohn, Kalamazoo, Mich.) was then positioned over the craniotomy and the temporails muscle and skin were closed in two layers. Animals were allowed to recover from anesthesia under a heating lamp and then were returned to their cages. The animals were sacrificed 24 hours following MCAO and the brains were prepared from reactive histologic examination.

Measurements of Ischemic Damage

Following the neurologic evaluation (24 hours after surgery) rats were euthanized with an overdose of sodium pentobarbital. Within 2–3 min, brains were removed and six coronal forebrain slices (2 mm thick) were made from the level of the olfactory bulbs to the cortical-cerebellar junction using a rat brain slicer [(59); Zivic-Miller Laboratories Inc., Allison Park, Pa.]. These forebrain slices then were immersed immediately in a 1% solution of triphenyltetrazolium chloride (TTC) in phosphate buffer at 37° C. for 20–30 min (6.78). Strained tissues then were fixed by filtration in 10% phosphate buffered formalin. The two sides of each TTC-strained section were photographed in colour using a polaroid camera These photographs were analyzed for the quantification of ischemic damage using an image analysis system (Amersham RAS 3000; Loats Associates, Inc.). Morphological changes following surgery were evaluated in the entire forebrain (total of 11 planar surfaces) for each animal. The 11 planar images were planar surfaces) for each animal. The 11 planar images were obtained from each side of the six 2 mm thick sections and correspond approximately to 1 mm section surfaces from +1 mm to −5 mm from bregma (97) and include the complete forebrain. These planar image surfaces (from the photographs) were digitized and used in the Image Analysis System for planimetry determination of infarct size and swelling. Two parameters of ischemic damage due to MCAO were determined for each slice as described previously (2,4,98,122). "Hemispheric swelling" was expressed as the percent increase in size of the ipsilateral (i.e., surgery side) hemisphere over the contralateral (normal) hemisphere and was calculated as:

$$\text{Percent Hemispheric Swelling} = \frac{\text{Ipsilateral Hemisphere Area} - \text{Contralateral Hemisphere Area}}{\text{Contralateral Hemisphere Area}} \times 100$$

"Infarct size" which was expressed as the percent infarcted tissue in reference to the contralateral (normal) hemisphere and was calculated as:

$$\text{Percent Hemispheric Infarct Size} = \frac{\text{Infarct area}}{\text{Contralateral Hemisphere Area}} \times 100$$

The swelling and infarct size were expressed in reference to the contralateral hemisphere (i.e., ipsilateral ischemic damage was normalized to the normal contralateral hemisphere). These parameters were determined for each slice to evaluate the profile of damage throughout the forebrain (i.e., "fore-brain profile") and for "total" forebrain changes by using the sum of all individual slice data in these formulas.

The occurrence of brain edema asociated with hemispheric swelling following MCAO was determined by comparison of wet/dry weight as described previously (45,118). Rats were sacrificed by an overdose of sodium pentobarbital 24 hours after sham or MCAO surgery. The brains were quickly removed, the forebrain isolated at the cerebellar cortical junction and cut into two hemispheres, and each forebrain hemisphere measured on a Mettler Types H5 chemical balance (Mettler Instruments Corp, Hightstown, N.J.) within 2 min after decapitation. The dry weight was measured on the same scale after drying the hemisphere in an over at 80° C. for 48–72 hours. The water content of each hemisphere was calculated as the difference between the wet and dry weight as a percent fraction from the wet weight:

$$\text{Percent Water Content} = \frac{\text{Wet Weight} - \text{Dry Weight}}{\text{Wet Weight}} \times 100$$

a) Mongolian Gerbil Test

The compound of EXAMPLE 66 significantly increased CA1 neuronal survival one week after transient (6.5 min) forebrain ischaemia when administered either one hour pre-ischaemic event and 2 hours post ischaemic event using a dose of 3 mg/Kg.

b) MCAO method (on following page)

Effects of Example 66 on PMCAO in SHR Rats
6 day study P.O. (b.i.d.)

| Group | N | % Hemispheric infarct | Infarct Volume (mm³) | NG | HLP |
|---|---|---|---|---|---|
| Vehicle Control | 24 | × 15.3 SE 1.1 | × 90.2 SE 6.5 | × 1.4 SE 0.1 | × 0.4 SE 0.1 |
| Example 66 0.15 mg/kg | 6 | × 15.8 SE 1.8 | × 91.2 SE 11.1 | × 1.5 SE 0.2 | × 0.5 SE 0.2 |
| Example 66 0.3 mg/kg | 12 | × 14.3 SE 1.1 | × 83.5 5E 6.3 | × 1.2 SE 0.1 | × 0.12 SE 0.1 |
| Example 66 1.0 mg/kg | 15 | × 127 SE 1.2 | × 75.8 SE 6.7 | × 1.7 SE 0.1 | × 0.6 SE 0.1 |
| Example 66 3.0 mg/kg | 14 | × 12.3 SE 1.3 | × 73.7 SE 7.8 | × 1.7 SE 0.1 | × 0.5 SE 0.1 |
| Example 66 10 mg/kg | 10 | × 8.2* SE 1.6 | × 47.6* SE 8.8 | × 1.8 SE 0.1 | × 0.6 SE 0.2 |

*Significant $p < 0.05$.

We claim:

1. A method of treatment of anxiety disorders treatable with anti-convulsive agents which comprises administering to the sufferer in need thereof an effective amount of a compound wherein the compound is:

trans-6-ethyl-3,4-dihydro-2,2-dimethyl-4S-(2-pyridinylcarbonyl)amino-2H-1-benzopyran-3R-ol, trans-6-cyano-4S-(5-chloro-2-thiophenylcarbonylamino)-3,4-dihydro-2,2-dimethyl-2H-1-benzopyran-3R-ol, trans-4-(4-chlorobenzoylamino)-6-cyano-3,4-dihydro-2,2-dimethyl-2H-1-benzopyran-3-ol, trans-6-cyano-3,4-dihydro-2,2-dimethyl-4S-(4-nitrobenzoylamino)-2H-1-benzopyran-3R-ol, trans-4S-(4-aminobenzoylamino)-6-cyano-3,4-dihydro-2,2-dimethyl-2H-1-benzopyran-3R-ol, trans-6-cyano-4-(4-trifluoromethyl-benzoylamino)-3,4-dihydro-2,2-dimethyl-2H-1-benzopyran-3-ol, trans-6-Cyano-4-(2-iodobenzoylamino)-3,4-dihydro-2,2-dimethyl-2H-1-benzopyran-3-ol, trans-4-(3-Bromo-4-fluorobenzoylamino)-6-ethyl-3,4-dihydro-2,2-dimethyl-2H-1-benzopyran-3-ol, trans-4S-(3-Bromo-4-fluorobenzoylamino)-6-ethyl-3,4-dihydro-2,2-dimethyl-2H-1-benzopyran-3R-ol, trans-6-Ethyl-4-(3-trifluoro-4-fluorobenzoylamino)-3,4-dihydro-2,2-dimethyl-2H-1-benzopyran-3-ol, trans-4-(4-Bromobenzoylamino)-6-ethyl-3,4-dihydro-2,2-dimethyl-2H-1-benzopyran-3-ol, trans-4-(3-Fluoro-4-methylbenzoylamino)-6-ethyl-3,4-dihydro-2,2-dimethyl-2H-1-benzopyran-3-ol, trans-4-(3-fluoro-4-methoxyamino)-6-ethyl-3,4-dihydro-2,2-dimethyl-2H-1-benzopyran-3-ol, trans-4-(3-Chloro-4-fluorobenzoylamino)-6-ethyl-3,4-dihydro-2,2-dimethyl-2H-1-benzopyran-3-ol, trans-4-(3-bromobenzoylamino)-6-ethyl-3,4-dihydro-2,2-dimethyl-2H-1-benzopyran-3-ol, trans-4-(4-Fluoro-3-methylbenzoylamino)-6-ethyl-3,4-dihydro-2,2-dimethyl-2H-1-benzopyran-3-ol, trans-6-Acetyl-4-(3-bromo-4-fluorobenzoylamino)-3,4-dihydro-2,2-dimethyl-2H-1-benzopyran-3-ol, trans-6-Acetyl-4-(3-bromobenzoylamino)-3,4-dihydro-2,2-dimethyl-2H-1-benzopyran-3-ol, trans-6-Acetyl-4-(2-bromobenzoylamino)-3,4-dihydro-2,2-dimethyl-2H-1-benzopyran-3-ol, trans-6-Acetyl-4-(5-bromo-2-furanoylamino)-3,4-dihydro-2,2-dimethyl-2H-1-benzopyran-3-ol, trans-6-Acetyl-4-(2-azidobenzoylamino)-3,4-dihydro-2,2-dimethyl-2H-1-benzopyran-3-ol, trans-6-Acetyl-4-(3-azidobenzoylamino)-3,4-dihydro-2,2-dimethyl-2H-1-benzopyran-3-ol, trans-6-Acetyl-4-(3-chlorobenzoylamino)-3,4-dihydro-2,2-dimethyl-2H-1-benzopyran-3-ol, trans-6-Acetyl-4-(3-trifluoromethylbenzoylamino)-3,4-dihydro-2,2-dimethyl-2H-1-benzopyran-3-ol, trans-6-Acetyl-4-benzoylamino-3,4-dihydro-2,2-dimethyl-2H-1-benzopyran-3-ol, trans-6-Acetyl-4-(2-iodobenzoylamino)-3,4-dihydro-2,2-dimethyl-2H-1-benzopyran-3-ol, trans-6-Acetyl-4-(3-iodobenzoylamino)-3,4-dihydro-2,2-dimethyl-2H-1-benzopyran-3-ol, trans-6-Acetyl-4-(2-nitrobenzoylamino)-3,4-dihydro-2,2-dimethyl-2H-1-benzopyran-3-ol, trans-6-Acetyl-4-(2-chlorobenzoylamino)-3,4-dihydro-2,2-dimethyl-2H-1-benzopyran-3-ol, trans-6-Acetyl-4-(3-cyanobenzoylamino)-3,4-dihydro-2,2-dimethyl-2H-1-benzopyran-3-ol, trans-6-Acetyl-4-(4-chlorobenzoylamino)-3,4-dihydro-2,2-dimethyl-2H-1-benzopyran-3-ol, trans-6-Acetyl-4-(2-aminobenzoylamino)-3,4-dihydro-2,2-dimethyl-2H-1-benzopyran-3-ol, trans-6-Acetyl-4-(3-nitrobenzoylamino)-3,4-dihydro-2,2-dimethyl-2H-1-benzopyran-3-ol, trans-6-Acetyl-4-(2-trifluoromethoxybenzoylamino)-3,4-dihydro-2,2-dimethyl-2H-1-benzopyran-3-ol, trans-6-Acetyl-4S-(2-chlorobenzoylamino)-3,4-dihydro-2,2-dimethyl-2H-1-benzopyran-3R-ol, trans-6-Acetyl-4-(2,3-dichlorobenzoylamino)-3,4-dihydro-2,2-dimethyl-2H-1-benzopyran-3-ol, trans-6-Acetyl-4-(2-chloro-4-fluorobenzoylamino)-3,4-dihydro-2,2-dimethyl-2H-1-benzopyran-3-ol, trans-6-Acetyl-4S-(2-chloro-4-fluorobenzoylamino)-3,4-dihydro-2,2-dimethyl-2H-1-benzopyran-3R-ol, trans-6-Acetyl-4S-(2-trifluoromethylbenzoylamino)-3,4-dihydro-2,2-dimethyl-2H-1-benzopyran-3R-ol, trans-6-Acetyl-4S-(3-chlorobenzoylamino)-3,4-dihydro-2,2-dimethyl-2H-1-benzopyran-3R-ol, trans-6-Acetyl-4-(3-chlorothiophen-2-carbonylamino)-3,4-dihydro-2,2-dimethyl-2H-1-benzopyran-3-ol, trans-6-Acetyl-4S-(2-chlorothiophen-3-carbonylamino)-3,4-dihydro-2,2-dimethyl-2H 1 -benzopyran-3R-ol, trans-6-Acetyl-4-(5-bromothiophen-2-carbonylamino)-3,4-dihydro-2,2-dimethyl-2H-1-benzopyran-3-ol, trans-6-Acetyl-4-(3,5-dibromobenzoylamino)-3,4-dihydro-2,2-dimethyl-2H-1-benzopyran-3-ol, trans-6-Acetyl-4-(2-chloro-6-fluorobenzoylamino)-3,4-dihydro-2,2-dimethyl-2H-1-benzopyran-3-ol, trans-6-Acetyl-4-(3-chloro-2-fluorobenzoylamino)-3,4-dihydro-2,2-dimethyl-2H-1-benzopyran-3-ol, trans-6-Acetyl-4-(2,6-dichlorobenzoylamino)-3,4-dihydro-2,2-dimethyl-2H-1-benzopyran-3-ol, trans-6-Acetyl-4-(2-azido-4-fluorobenzoylamino)-3,4-dihydro-2,2-dimethyl-2H-1-benzopyran-3-ol, trans-6-Acetyl-4-(2-azido-5-fluorobenzoylamino)-3,4-dihydro-2,2-dimethyl-2H-1-benzopyran-3-ol, trans-6-Acetyl-4S-(2-methylbenzoylamino)-3,4-dihydro-2,2-dimethyl-2H-1-benzopyran-3R-ol, trans-6-Acetyl-4S-(4-methylbenzoylamino)-3,4-dihydro-2,2-dimethyl-2H-1-benzopyran-3R-ol, trans-6-Acetyl-4-(2-chloro-3-nitrobenzoylamino)-3,4-dihydro-2,2-dimethyl-2H-1-benzopyran-3-ol, trans-6-Acetyl-4-(2-chloro-5-nitrobenzoylamino)-3,4-dihydro-2,2-dimethyl-2H-1-benzopyran-3-ol, trans-6-Acetyl-4-(2-methoxybenzoylamino)-3,4-dihydro-2,2-dimethyl-2H-1-benzopyran-3-ol, trans-6-Acetyl-4S-(3-chloro-4-fluorobenzoylamino)-3,4-dihydro-2,2-dimethyl-2H-1-benzopyran-3R-ol, trans-6-Acetyl-4-(2-chloro-4-hydroxybenzoylamino)-3,4-dihydro-2,2-dimethyl-2H-1-benzopyran-3-ol, trans-6-Acetyl-4S-(2,3-dichlorobenzoylamino)-3,4-dihydro-2,2-dimethyl-2H-1-benzopyran-3R-ol, and trans-6-Acetyl-3,4-dihydro-2,2-dimethyl-4-(2-pyrazinecarboxybenzoylamino)-2H-1-benzopyran-3-ol;

or a pharmaceutically acceptable salt thereof.

2. The method according to claim 1 wherein said disorder which is treatable with anti-convulsive agents is epilepsy.

* * * * *